(12) United States Patent
O'Sullivan et al.

(10) Patent No.: US 11,896,784 B2
(45) Date of Patent: Feb. 13, 2024

(54) SECUREMENT DEVICE FOR PIPES, CABLES OR CATHETERS

(71) Applicant: University of Limerick, Limerick (IE)

(72) Inventors: Aidan G. O'Sullivan, Tralee (IE); Leonard W. O'Sullivan, Clonlara (IE); Eoin J. White, Waterford (IE); Niall Deloughry, Limerick (IE); Austin Stack, Adare (IE)

(73) Assignee: University of Limerick, Limerick (IE)

( * ) Notice: Subject to any disclaimer, the term of this patent is extended or adjusted under 35 U.S.C. 154(b) by 486 days.

(21) Appl. No.: 17/259,490

(22) PCT Filed: Jul. 4, 2019

(86) PCT No.: PCT/EP2019/068012
§ 371 (c)(1),
(2) Date: Jan. 11, 2021

(87) PCT Pub. No.: WO2020/011647
PCT Pub. Date: Jan. 16, 2020

(65) Prior Publication Data
US 2021/0316118 A1   Oct. 14, 2021

(30) Foreign Application Priority Data
Jul. 12, 2018  (GB) .................................. 1811443

(51) Int. Cl.
*A61M 25/02* (2006.01)
(52) U.S. Cl.
CPC ....... *A61M 25/02* (2013.01); *A61M 2025/024* (2013.01); *A61M 2025/028* (2013.01); *A61M 2025/0273* (2013.01)

(58) Field of Classification Search
CPC ............ A61M 25/02; A61M 2025/024; A61M 2025/0273; A61M 2025/028;
(Continued)

(56) References Cited

U.S. PATENT DOCUMENTS 3,624,673 A * 11/1971 Merchant ................ D06F 55/02
                                                       24/561
7,223,256 B2   5/2007 Bierman
(Continued)

FOREIGN PATENT DOCUMENTS

| EP | 2574366 A1 | 4/2013 |
| EP | 2574367 A1 | 4/2013 |

(Continued)

OTHER PUBLICATIONS

International Search Report and Written Opinion in International Application No. PCT/EP2019/068012, dated Oct. 17, 2019 (15 pages).

*Primary Examiner* — Brandy S Lee
*Assistant Examiner* — Phoebe Anne Staton
(74) *Attorney, Agent, or Firm* — Bookoff McAndrews, PLLC (57) ABSTRACT

A securement device 1 for securely attaching tubular articles 2 to surfaces comprising an anchor pad 3 for placing the securement device 1 on the surface, a substantially cylindrical base 4 on the anchor pad 3 and a screw cap 5 rotatably mountable on the base 4 at a screw mounting 6 defined between the base 4 and the screw cap 5 between an article receiving position and an article gripping position in which radial pressure is applied to the article 2 placed in the securement device 1 to securely hold the article 2 without the use of external adhesive fixings and prevent micro-pistoning of the article 2.

20 Claims, 7 Drawing Sheets

(58) Field of Classification Search
CPC .. A61M 2025/0266; A61M 2025/0246; A61M 2025/0293; A61M 39/1011; A61M 2039/1027; A61M 2039/1033; A61M 2025/0253; A61M 2025/026; A61M 5/1418; F16G 11/101; H02G 3/32; B65D 2215/02; B65D 2215/04; A61B 1/0014
See application file for complete search history.

(56) References Cited

U.S. PATENT DOCUMENTS

| | | | |
|---|---|---|---|
| 2004/0204684 A1 | 10/2004 | Bierman | |
| 2005/0033268 A1* | 2/2005 | Decaria | A61J 15/0026 604/533 |
| 2010/0298778 A1 | 11/2010 | Bracken et al. | |
| 2012/0271239 A1* | 10/2012 | Andino | A61M 5/1418 604/174 |
| 2013/0079721 A1* | 3/2013 | Mizoguchi | A61M 25/02 604/174 |
| 2014/0200517 A1 | 7/2014 | Humphries et al. | |
| 2014/0276542 A1 | 9/2014 | Ciccone | |
| 2014/0276544 A1 | 9/2014 | Aviles | |
| 2021/0106789 A1* | 4/2021 | Molina | A61M 39/20 |

FOREIGN PATENT DOCUMENTS

| | | | |
|---|---|---|---|
| FR | 3051118 A1 * | 11/2017 | |
| FR | 3051118 A1 | 11/2017 | |
| WO | WO 2011/044293 A1 | 4/2011 | |

* cited by examiner

SECUREMENT DEVICE FOR PIPES, CABLES OR CATHETERS

CROSS-REFERENCE TO RELATED APPLICATION(S)

This patent application is the U.S. National Phase Entry under 35 U.S.C. § 371 of International Application No. PCT/EP2019/068012, filed on Jul. 4, 2019, which claims priority to GB Patent Application No. 1811443.9, filed on Jul. 12, 2018.

This invention relates to a securement device for securely attaching an article to a surface.

BACKGROUND OF THE INVENTION

In general, it can be difficult to securely attach articles to surfaces without resorting to the use of secondary (adhesive) fixings and the like. For example, the medical treatment of patients commonly involves the use of percutaneously inserted medical cannulas such as medical lines or catheters to monitor vital functions, administer high volume or aggressive medications, to direct fluids into the bloodstream, or facilitate access for dialysis. However, any catheter or other medical article inserted in the human body for medical treatment is susceptible to serious complications such as migration, dislodgement, thrombosis, occlusion and infection. For example, accidental dislodgement can occur in between 5% and 31% of catheters and can arise when a catheter experiences a sudden external force from being pulled or accidentally caught by another object. Moreover, accidental motion or "micro-pistoning" can occur with cannulas i.e. movement of a catheter in and out of a vein in a pistoning action. Even a small amount of catheter motion can be a contributing factor to negative complications in patients with central venous catheters or any other cannula.

Accordingly, in an attempt to minimise cannula movement and micro-pistoning clinicians typically employ adhesive bandages, plasters or surgical tape to attach catheters and the like to a patient in a stationary manner.

The use of adhesive bandages, plasters and the like to hold cannulas in place can result in a significant build-up of adhesive residue on the cannulas, their associated tubing and patients—particularly where regular re-positioning of the cannula is required e.g. in dialysis patients. Residue build-up on catheters and tubing can be particularly difficult to remove giving rise to increased infection risks while residue build-up can also weaken the structure of catheters.

Moreover, such ad-hoc and improvised methods are generally unreliable and undesirable movement and micro-pistoning of medical articles can still take place to the detriment of the patient.

Dedicated securement devices for catheters are also known. However, the known devices also suffer from a number of disadvantages. For example, many known devices secure catheters significant distances from the catheter entry site—a distance of 40 mm being typical. As a result, while the securement device may protect the catheter from catastrophic dislodgment if pulled, hysteresis created between the entry site and the securement device can still be sufficient to allow micro-pistoning to occur.

Other known securement devices can also be invasive e.g. by employing two small metallic legs which are implanted into the skin of the patient at the entry site to secure the securement device in situ. However, such an invasive approach is currently only compatible with peripherally inserted central (PICC) catheters and cannot be used for other applications.

U.S. Pat. Nos. 7,223,256, 2010/0298778, 2014/0200517, 2014/0276542, 2004/0204684, 2014/0276544 also describe various dedicated securement devices for catheters and the like. However, as with the ad hoc devices described above, the dedicated securement devices of the prior art cannot be easily repositioned without giving rise to adhesive residues. European Patent Specification Nos. 2574366 and 2574367 also describe catheter fixing devices in which catheters must be squeezed to be held in place which can interfere with the performance of the catheter. Moreover, all the dedicated securement devices of the prior art rely on relatively complex catheter holding structures and still fail to effectively eliminate micro-pistoning while the complex structures employed limit the use of the prior art securement devices to particular catheter types and sizes.

SUMMARY OF THE INVENTION

Accordingly, in a first aspect, the invention provides a securement device for attaching an article to a surface comprising:
an anchor pad attachable to a surface;
a base on the anchor pad for receiving the article, and
a cap mountable on the base at a mounting defined between the base and the cap, the cap being rotatable on the base between an article receiving position and an article gripping position and comprising a slot for receiving an article in the article receiving position and gripping the article in the article gripping position.

Preferably, the base defines a channel for receiving the article.

In one embodiment, the base comprises a substantially cylindrical base.

Preferably, the slot comprises an article receiving portion complementary with the channel for receiving the article in the article receiving position. More preferably, the slot comprises a substantially helical slot portion for gripping an article with a radial force in the article gripping position. Most preferably, the slot comprises first and second oppositely disposed substantially helical slot portions in a sidewall of the cap.

Advantageously, the helical slot portions comprise an upright slot element (i.e. substantially orthogonal to the surface) and a substantially horizontal slot element (i.e. substantially parallel to the surface) contiguous with the upright slot element in the sidewall. Preferably, the substantially horizontal slot element is continuously tapered towards a slot end in the sidewall.

Preferably, the mounting comprises a screw mounting to impart a downward compressive force on an article in the article gripping position. More preferably, the screw mounting comprises a thread on the base.

Suitably, the thread comprises first and second oppositely disposed substantially helical threads on the base. Preferably, the thread comprises a groove-like thread.

Optionally, the screw mounting comprises at least one lug on the cap insertable in the thread.

Preferably, the thread further comprises at least one stop abuttable against the at least one lug.

Optionally, the securement device further comprises a lock to prevent unauthorised or accidental release of the securement device. Preferably, the lock comprises a push to release lock in the cap such as a child proof lock of the type found on medicine containers.

In a further embodiment of the invention, the securement device comprises a secondary fixing clasp for clasping the article in place.

Preferably, the secondary fixing clasp is mounted on the anchor pad. More preferably, the secondary fixing clasp is mounted on a secondary anchor pad portion spaced apart from a primary anchor pad portion. Most preferably, the primary anchor pad portion is connected with the secondary anchor pad portion by an anchor pad web portion extending between the primary anchor pad portion and the secondary anchor pad portion.

Preferably, the anchor pad comprises an adhesive for adhering the securement device to a surface.

Suitably, the anchor pad comprises a release film on the adhesive.

In a preferred embodiment of the invention, the securement device comprises a securement device for attaching a medical article to a patient.

The invention generally therefore relates to a securement device for attaching an article to a surface comprising an anchor pad attachable to a surface; a base on the anchor pad for receiving the article, and a cap mountable on the base at a mounting defined between the base and the cap, the cap being rotatable on the base between an article receiving position and an article gripping position.

The base can comprise a substantially cylindrical base defining a channel for receiving the article. In a preferred variant, the cap comprises a slot for receiving an article in the article receiving position and gripping the article in the article gripping position.

The securement device of the invention securely holds articles in place on a surface and is adapted to reversibly hold (elongate) cylindrical or tubular articles in place on surfaces so that the articles can be repositioned as required without giving rise to a build-up of adhesive residues on the articles.

The securement device is particularly adapted to hold medical articles such as catheters, lines, intravenous drips, surgical drains and cables such as E.C.G. cables in position on a patient. The securement device can be used to position and reposition the medical articles as required without employing adhesive bandages and plasters so that no build-up of adhesive residue occurs on the medical articles.

Accordingly, the securement device of the invention minimises the risk of infection caused by adhesive residues whilst also ensuring that the structural integrity of the medical article is maintained. The securement device is therefore particularly suitable for use with medical articles requiring frequent repositioning e.g. dialysis catheters.

The securement device of the invention also inhibits axial motion such as micro-pistoning of the medical article. More particularly, the radial force applied by the rotatable securement device of the invention to tubular medical articles such as so catheters eliminates the need to use adhesive bandages, plasters or surgical tape, whilst providing a rigid securement to prevent movement and/or dislodgment. The dedicated medical line securement device therefore reduces the risk of related complications by reducing movement such as micro-pistoning whilst allowing consistent and rapid access to the line by clinicians. The securement device of the invention can also be positioned adjacent entry sites on patients so that catheter hysteresis which can give rise to micro-pistoning is reduced or eliminated.

The jaw-like continuously tapered slot of the securement device for gripping tubular articles allows the securement device to grip a range of tubing/cabling sizes so that non-standard tubing/cabling can be gripped i.e. no specific tubing size graduation is required. This also allows for confident securing of tubular articles which may have swelled or changed dimension from use overtime and which, as a result, may not adhere to their original manufactured size specification—this can be a particular problem with catheters. Accordingly, in contradistinction with known dedicated securement devices, a securement device of the invention can function effectively with a range a tubular articles.

In addition to the radial force applied by the tapered slot, downward rotational movement of the screw cap on the base of the securement device of the invention results in a downward compressive force on articles so that the articles are urged or pulled tightly into the base to further enhance secure gripping of the article.

The securement device is also suitable for use with other cylindrical or tubular non-medical articles such as computer cabling, machine tubing, electrical cabling, hydraulic/pneumatic cabling and oil cabling where an effective (repositionable) grip is required that does not damage the articles and does not rely on the use of adhesives.

The securement device of the invention is also of relatively simple construction with only three components making it easy and cost-efficient to manufacture.

BRIEF DESCRIPTION OF THE DRAWINGS

The invention will now be described, by way of example only, with reference to the accompanying drawings in which.

DETAILED DESCRIPTION OF THE INVENTION

As shown in FIGS. 1 to 9 of the accompanying drawings, a first embodiment of a securement device 1 in accordance with the invention for securely attaching a medical article such as a catheter 2 to a patient is generally made up of an anchor pad 3 for placing the securement device 1 on the patient, a base in the form of a substantially cylindrical base 4 on the anchor pad 3 and a screw cap 5 rotatably mountable on the base 4 at a (screw) mounting 6 defined between the base 4 and the screw cap 5 between a catheter receiving position (shown in FIGS. 2, 4 and 6) and a catheter gripping position (shown in FIGS. 3, 5, 8 and 9) in which radial pressure is applied to the catheter 2 placed in the securement device 1 to securely hold the catheter 2 and prevent micro-pistoning of the catheter 2. The screw cap 5 can be moved repeatedly between the catheter receiving and catheter gripping positions so that the catheter 2 can be positioned, secured, repositioned and re-secured as needed without requiring the use of adhesive plasters, dressings and the like. As a result, adhesive residues do not build up on the catheter 2 so that the risk of infection is minimised and the structural integrity of the catheter 2 is not compromised.

Figure 1:
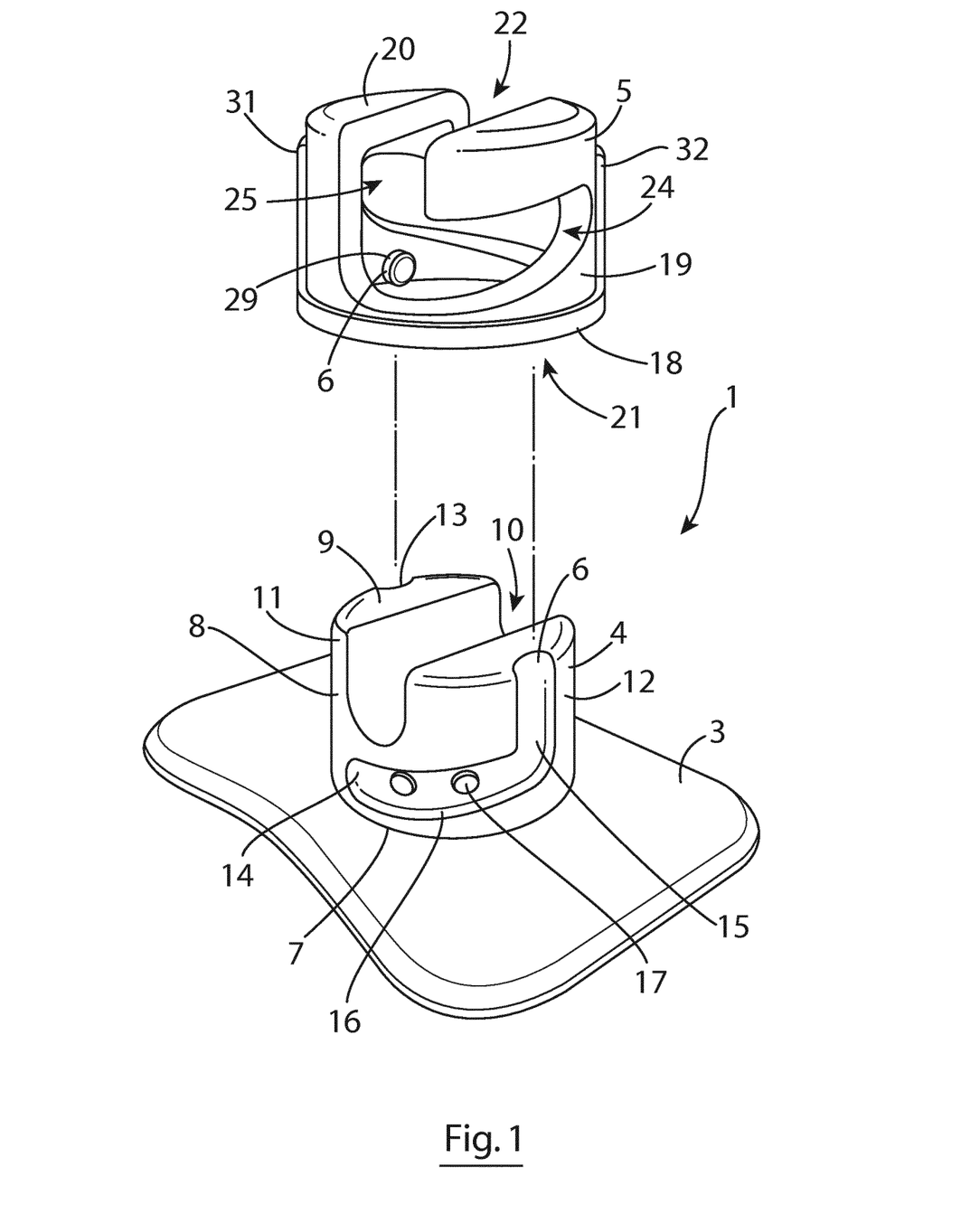
FIG. 1 is an exploded perspective view from above and one side of a first embodiment of a securement device of the invention for securely attaching a medical article such as a line or catheter to a patient made up of an anchor pad, a base in the form of a cylindrical base and a screw cap rotatably mountable on the base to apply radial pressure to a catheter (not shown) placed in the securement device to grip the catheter and prevent micro-pistoning of the catheter.
Figure 2:
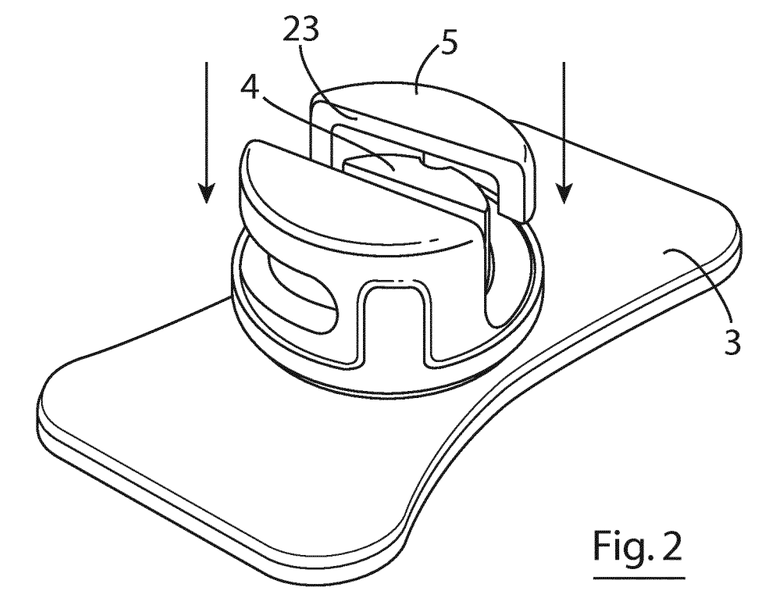
FIG. 2 is a perspective view from above and one side of the securement device of FIG. 1 with the screw cap mounted on the base in the direction indicated by the arrows in a catheter receiving position i.e. with the U-shaped catheter channel in the base and the transverse catheter insertion portion of the slot in the cap aligned to receive a catheter.
Figure 3:
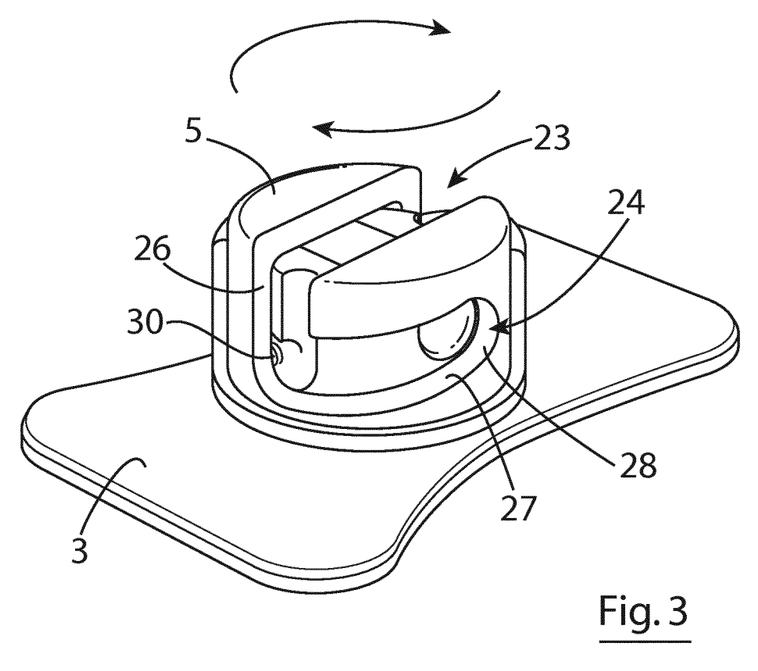
FIG. 3 is perspective view from above and one side of the securement device of FIG. 2 following clockwise rotation of the cap on the base in the direction indicated by the arrows into the catheter gripping position to apply a radial gripping force and a downward compressive gripping force to a catheter (not shown)

The cylindrical base 4 is made up of a circular bottom wall 7 in contact with the anchor pad 3, a sidewall 8 upstanding from the bottom wall 7 and a top face 9. The top face 9 is provided with a transverse U-shaped elongate channel 10 to sub-divide the sidewall 8 into a first sidewall portion 11 and an opposite second sidewall portion 12. The U-shaped channel 10 receives and holds a catheter 2 in the securement device 1 in use.

Externally, the first and second sidewall portions 11,12 are each provided with respective first and second oppositely disposed substantially helical groove-like threads 13,14 which form part of the mounting 6 defined between the base 4 and the screw cap 5. Each thread 13,14 has an upright thread portion 15 and a lower horizontal thread portion 16 contiguous with the upright thread portion 15. The lower horizontal portion 16 of each thread 13,14 is provided with spaced-apart stops 17 to provide resistance to prevent the screw cap 5 from free spinning on the base 4 and to provide haptic feedback during rotatable engagement of the screw cap 5 with the base 4. This shall be explained more fully below.

The screw cap 5 is complementary in size and shape with the base 4 and has a circular lower rim 18 with a circular sidewall 19 upstanding therefrom towards a top wall 20. The circular lower rim 18 defines a base opening 21 into which the base 4 is received by the screw cap 5 during mounting of the screw cap 5 on the base 4.

A tapered catheter slot 22 for receiving and gripping a catheter 2 is defined in the screw cap sidewall 19 and top wall 20. The catheter slot 22 is made up of a transverse catheter receiving portion 23 defined in the top wall 20 complementary with the transverse U-shaped catheter receiving channel 10 in the base 4 and first and second oppositely disposed substantially helical slot portions 24,25 for gripping a catheter 2 with a radial force defined in the sidewall 19. The helical slot portions 24,25 are each made up of an upright slot element 26 and a substantially horizontal slot element 27 contiguous with the upright slot element 26 defined in the cap sidewall 19. The horizontal slot elements 27 are continuously tapered towards a slot end 28 i.e. the catheter slot 22 narrows towards the slot end 28 so that the securement device 1 can accommodate and securely grip catheters 2, lines and the like of varying sizes in a jaw-like manner.

Internally, the screw cap 5 is provided with two oppositely disposed lugs 29,30 on the sidewall 19. The lugs 29,30 form part of the mounting 6 between the base 4 and the cap 5. More particularly, the lugs 29,30 are insertable in and co-operable with the first and second helical threads 13,14 respectively defined in the sidewall 8 of the cylindrical base 4 to allow rotatable mounting of the screw cap 5 on the base 4. As indicated above, the stops 17 in the lower horizontal thread portion 16 abut the lugs 29,30 to provide resistance to prevent free spinning of the screw cap 5 on the base 4 and to provide haptic feedback when rotating the screw cap 5 on the base 4. The spaced apart stops 17 co-operate with the lugs 29,30 to fix the screw cap 5 in position on the base 4 and allow for the securement device 1 to be size adjusted in accordance with the size of catheter 2 (or other article) placed in the securement device 1.

Externally, the screw cap 5 is provided with two oppositely disposed finger grips 31,32 on the screw cap sidewall 19 to facilitate manual gripping and rotation of the screw cap 5.

The anchor pad 3 of the securement device 1 is of conventional construction and has an adhesive layer 33 for adhering the anchor pad 3 to a patient. The adhesive layer 33 can be protected with a release film prior to use.

Figure 7:
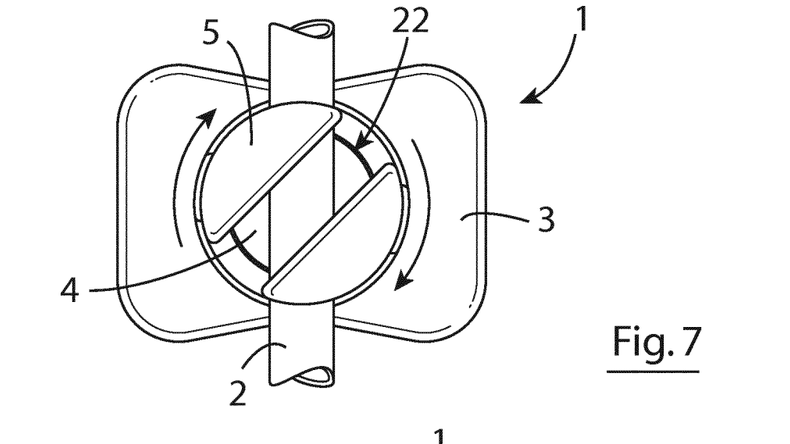
FIG. 7 is a top plan view of the securement device of FIG. 6 with the screw cap partially rotated in a clockwise manner in the direction indicated by the arrows between the catheter receiving and catheter gripping positions.
Figure 8:
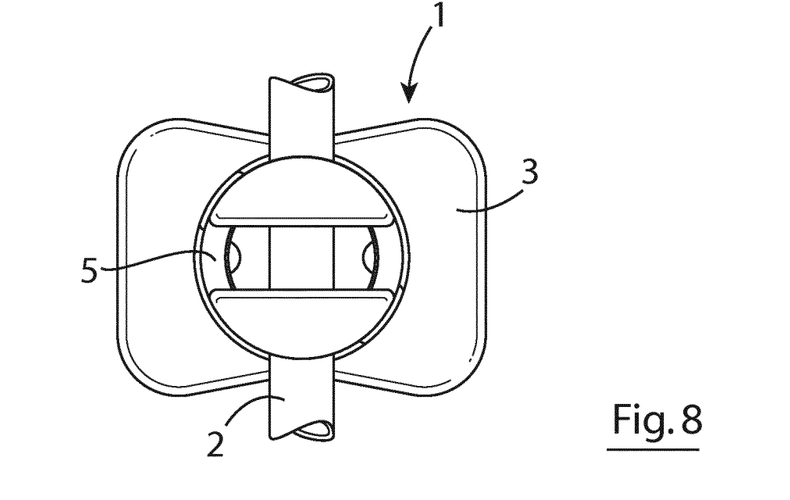
FIG. 8 is a top plan view of the securement device of FIG. 6 with the screw cap fully rotated into the catheter gripping position.
Figure 9:
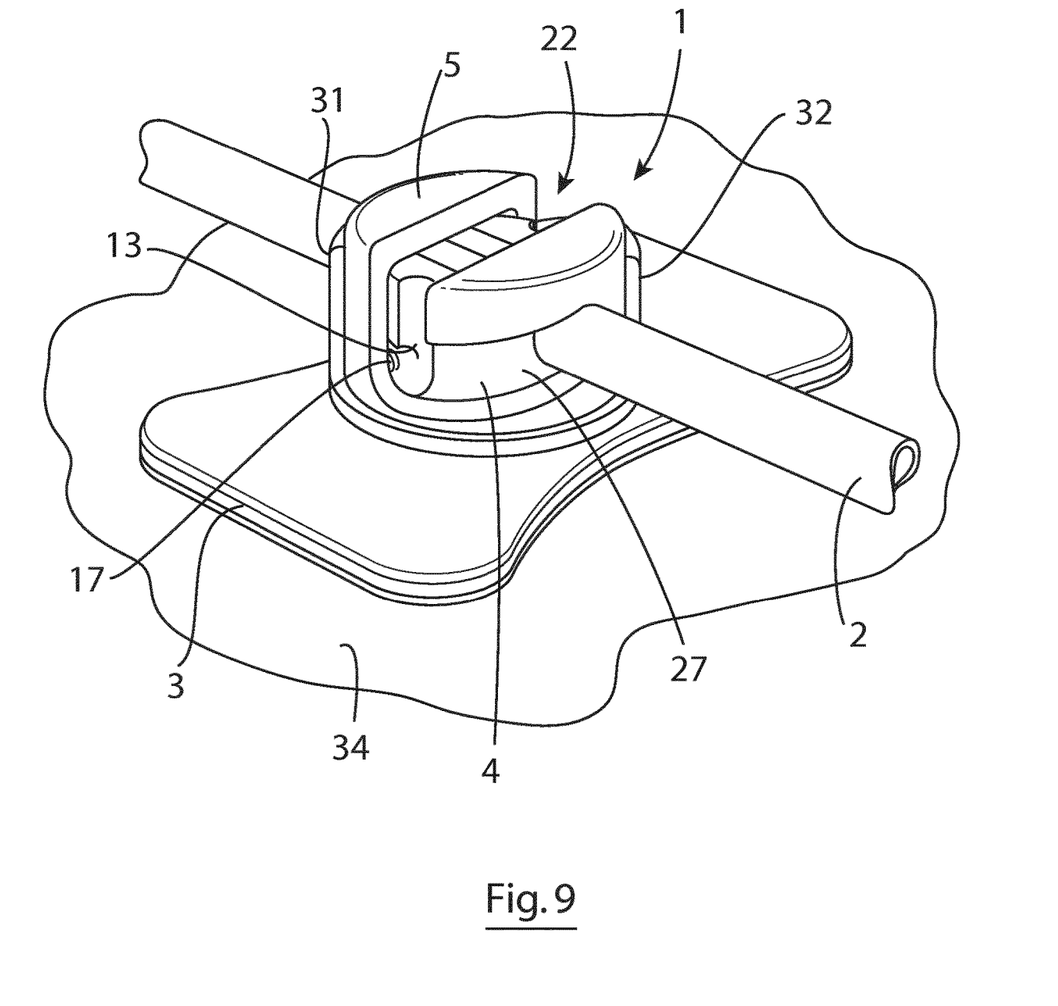
FIG. 9 is a perspective view from above and one side of the securement device and catheter of FIG. 8.

In use, the anchor pad 3 with the base 4 is placed on a patient's skin 34 as required. With the rotatable screw cap 5 in the catheter receiving position shown in FIGS. 2 and 4 (i.e. with the transverse catheter receiving portion 23 of the slot 22 in the screw cap 5 co-axially aligned with the transverse U-shaped catheter receiving channel 10 in the base 4), a catheter 2 is inserted into the catheter receiving channel 10 (see FIG. 6). The screw cap 5 is then gripped by a clinician at the grips 31,32 and rotated clockwise through 90° as shown in FIGS. 7, 8 and 9. The oppositely disposed helical catheter slot portions 24,25 of the catheter slot 22 therefore both slidably engage the catheter 2 in a jaw-like manner to apply radial pressure to the catheter 2 and securely grip the catheter 2. The catheter 2 is therefore gripped twice at two spaced apart locations by the securement device 1.

Figure 4:
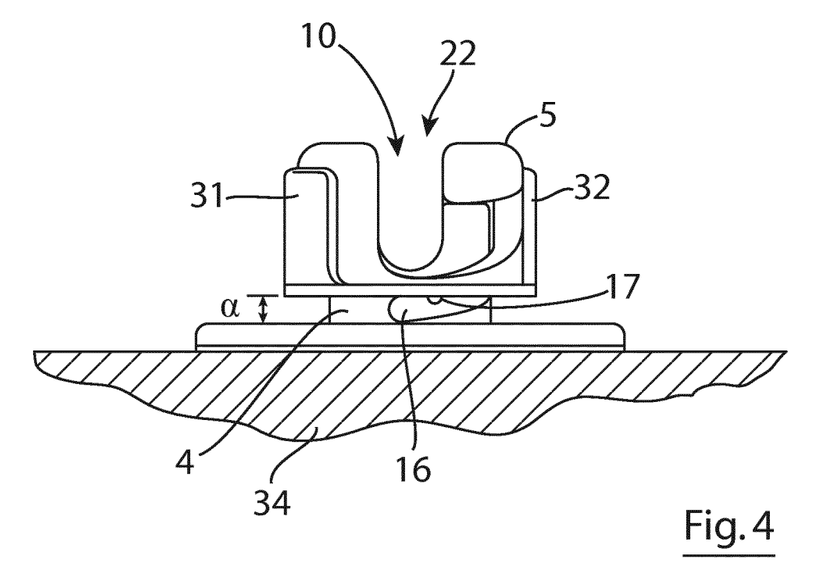
FIG. 4 is a side elevation of the securement device of FIG. 2 on a patient with the downward distance to be travelled by the screw cap on the base between the catheter receiving position and the catheter gripping position indicated by α.
Figure 5:
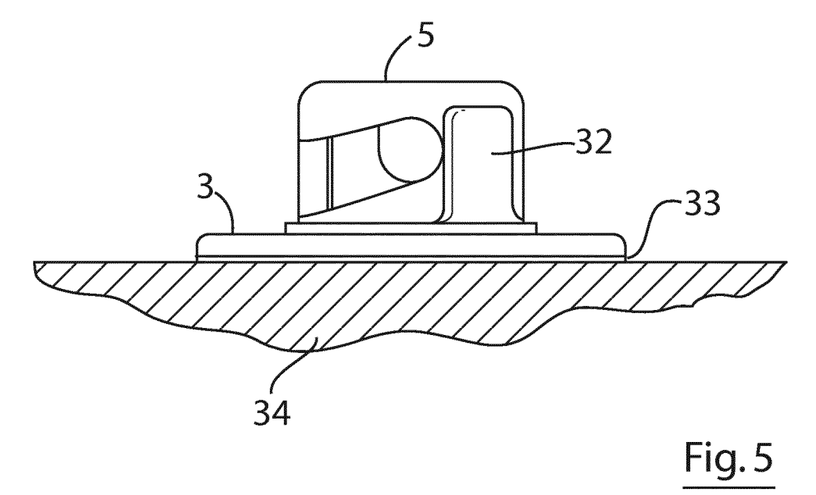
FIG. 5 is a side elevation of the securement device of FIG. 3 on a patient.
Figure 6:
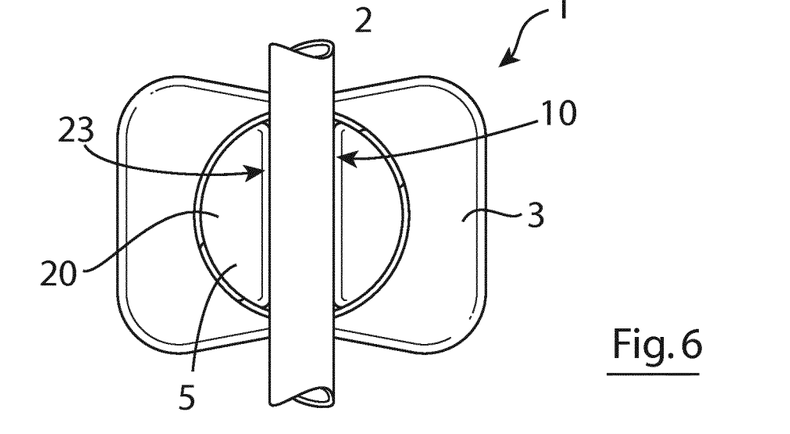
FIG. 6 is a top plan view of the securement device of FIG. 2 with a catheter inserted through the transverse catheter insertion portion of the slot in the cap into the U-shaped catheter channel in the base.

As shown particularly in FIGS. 4 and 5, rotation of the screw cap 5 on the base 4 causes the lugs 29,30 to travel downwards on the base 4 in the helical first and second threads 13,14 so that the screw cap 5 also applies a downward compressive force to the catheter 2 to urge the catheter 2 into the U-shaped channel 10 in the base 4 to further enhance gripping of the catheter 2. The downward distance, α, travelled by the screw cap 5 on the base 4, and hence the compressive force applied to the catheter 2, is determined by the dimensions of the securement device. However, a distance, α, of about 2 mm creates sufficient compressive force for most applications.

As indicated above, the stops 17 on the base 4 co-operate with the lugs 29,30 to prevent separation of the base 4 and the screw cap 5 whilst holding the screw cap 5 in place on the base 4 during application of the compressive force and providing haptic feedback during operation.

The above process is reversed in order to release the catheter 2 without damage to the catheter 2.

Figure 10:
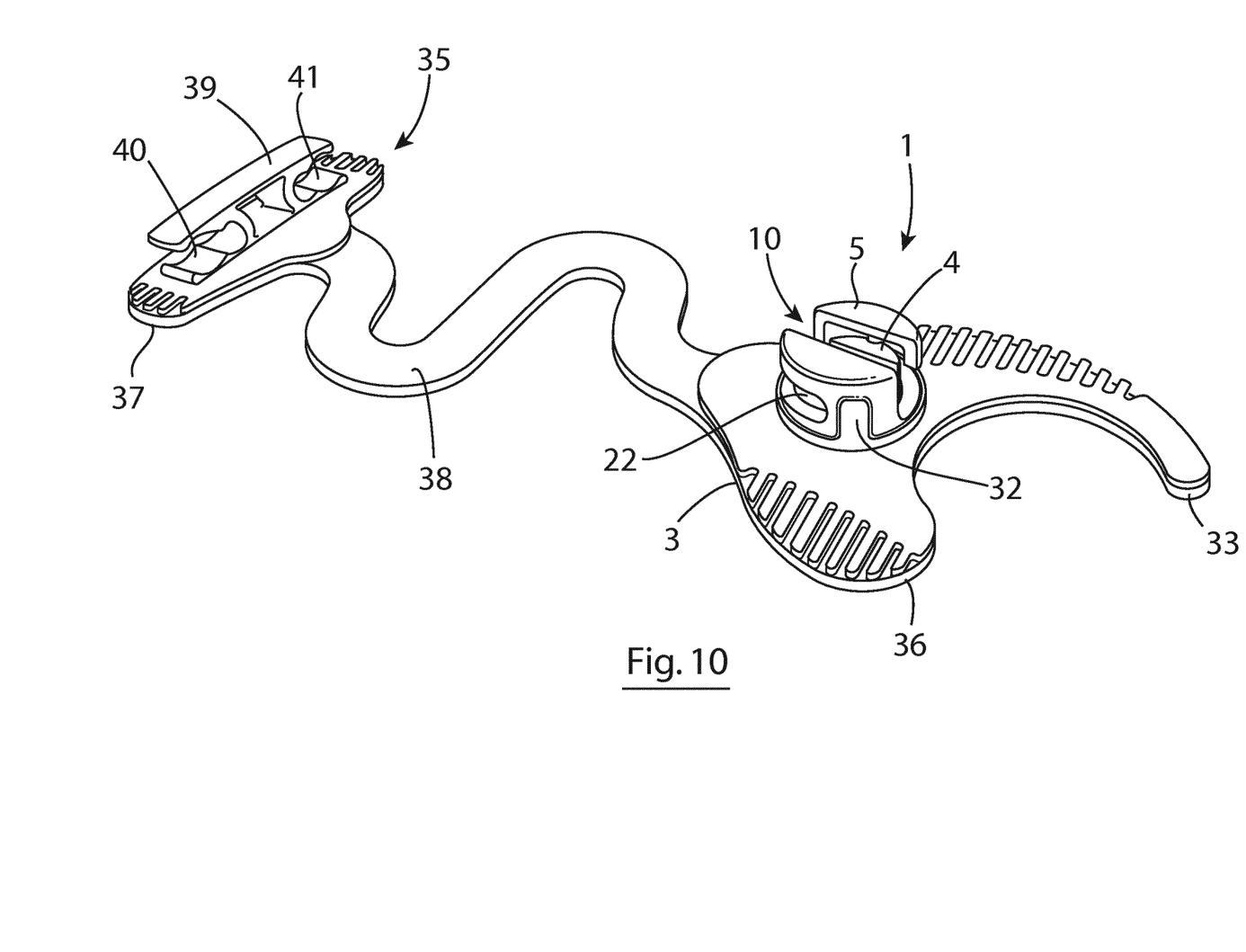
FIG. 10 is a perspective view from above and one side of a second embodiment of the securement device in which the securement device has a secondary or pre-fixing clasp on the anchor pad for clasping and tidying the catheter in place on the securement device.

FIGS. 9 and 10 show a second embodiment of a securement device 1 of the invention in which the securement device 1 has a secondary fixing clasp 35 on the anchor pad 3 for clasping and tidying a catheter 2 (not shown) in place on the securement device 1. The cylindrical base 4 and the screw cap 5 are as previously described in relation to the securement device 1 of FIGS. 1 to 9 and like numerals indicate like parts.

Figure 11:
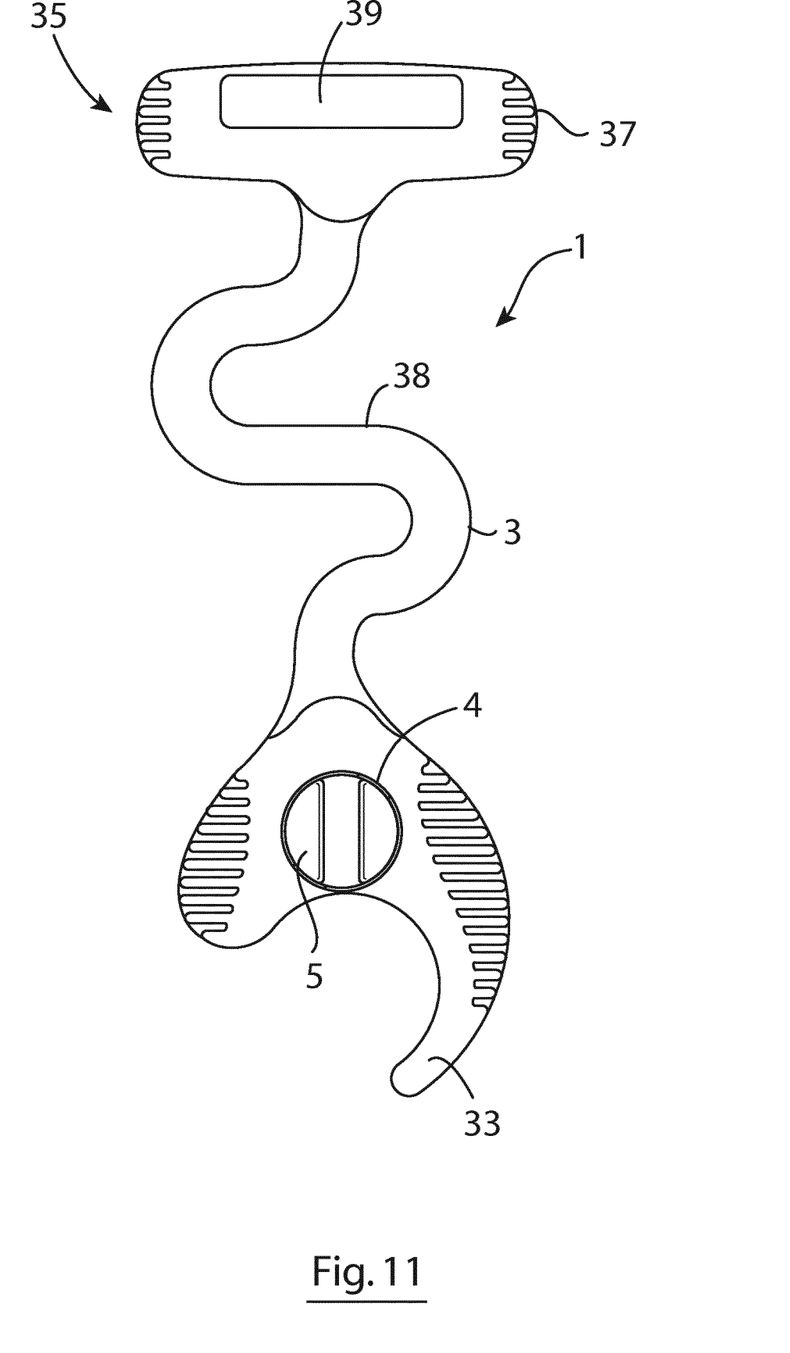
FIG. 11 is a top plan view of the securement device of FIG. 10.

In the present embodiment, the anchor pad 3 is shaped and contoured to define a primary anchor pad portion 36 on which the cylindrical base 4 of the securement device 1 is mounted and a secondary anchor pad portion 37, on which the secondary fixing clasp 35 is mounted, spaced apart from the primary anchor pad portion 36. The primary anchor pad portion 36 is connected with the secondary anchor pad portion 37 by a wave-shaped anchor pad web portion 38 which extends between the primary anchor pad portion 36 and the secondary anchor pad portion 37 and spaces the fixing clasp 35 a set distance from the cylindrical base 4.

The fixing clasp 35 has a fastener 39 for detachably fastening a catheter, or other tubular article, in the fixing clasp 35. In the present embodiment, the fastener 39 is made up of two oppositely disposed push-fit notches 40,41 defined in the fixing clasp 35 for holding catheters and the like. Catheters and the like are therefore clasped in the secondary fixing clasp 35 in addition to being secured between the base 4 and screw cap 5 of the securement device 1 so that the articles enjoy a double grip to further minimise movement of articles held in the securement device 1.

As indicated above, catheters and the like can be positioned and secured, repositioned and re-secured, repeatedly with the securement device 1 without requiring the use of adhesive plasters, dressings and the like so that adhesive residues do not build-up on the catheter 2. Use of the securement device 1 therefore minimises infection risk and ensures that the structural integrity of the catheter 2 is maintained.

The improved grip achieved by the securement device 1 of the invention prevents unwanted dislodgement of the catheter 2 and micro-pistoning in use.

If desired, the securement device 1 can be provided with a lock to prevent unauthorised or accidental release of the securement device e.g. outside a clinical setting or during movement. A suitable lock is a push to release lock incorporated into the securement device 1 requiring a pushing down action on the screw cap 5 before rotation to release the screw cap 5 from the base 4. Suitable lock mechanisms are to be found in the child-proof locks of medicine bottles and the like.

As will be appreciated by those skilled in the art, although the securement device 1 has been described in use with a catheter, the securement device 1 is suitable for use with a range of medical articles and particularly tubular medical articles such as catheters, lines, intravenous drips, surgical drains and cables such as E.C.G. cables. More generally, as indicated above, the securement device 1 is suitable for use with non-medical substantially tubular or cylindrical articles such as computer cabling, machine tubing, electrical cabling, hydraulic/pneumatic cabling and oil cabling where an effective (repositionable) grip is required that does not damage the articles and does not rely on the use of adhesives. Accordingly, the invention should not be construed as being limited to use with catheters only.

The invention claimed is:

1. A securement device for attaching a tubular medical article to a patient comprising:
an anchor pad attachable to the patient;
a base on the anchor pad for receiving the tubular medical article, and
a cap mountable on the base at a mounting defined between the base and the cap, the cap being rotatable on the base between a tubular medical article receiving position and a tubular medical article gripping position and comprising a slot for receiving the tubular medical article in the tubular medical article receiving position and gripping the tubular medical article in the tubular medical article gripping position
wherein the slot comprises first and second oppositely disposed substantially helical slot portions in a sidewall of the cap,
wherein each of the helical slot portions comprise an upright slot element and a helical slot element contiguous with the upright slot element in the sidewall,
wherein the upright slot elements are connected by a transverse slot element, and wherein the helical slot elements taper inwardly continuously towards a slot end in the sidewall.

2. A securement device as claimed in claim 1 wherein the base defines a channel for receiving the tubular medical article.

3. A securement device as claimed in claim 2, wherein the transverse slot portion is complementary with the channel for receiving the tubular medical article in the article receiving position.

4. A securement device as claimed in claim 1 wherein the base comprises a substantially cylindrical base.

5. A securement device as claimed in claim 1 wherein the mounting comprises a screw mounting to impart a downward compressive force on the tubular medical article in the tubular medical article gripping position.

6. A securement device as claimed in claim 5 wherein the screw mounting comprises a thread on the base.

7. A securement device as claimed in claim 6 wherein the thread comprises first and second oppositely disposed substantially helical threads on the base.

8. A securement device as claimed in claim 6 wherein the thread comprises a groove-like thread.

9. A securement device as claimed in claim 5 wherein the screw mounting comprises at least one lug on the cap insertable in the thread.

10. A securement device as claimed in claim 1 wherein the securement device comprises a secondary fixing clasp for clasping the tubular medical article in place.

11. A securement device as claimed in claim 10 wherein the secondary fixing clasp is mounted on the anchor pad.

12. A securement device as claimed in claim 10 wherein the secondary fixing clasp is mounted on a secondary anchor pad portion spaced apart from a primary anchor pad portion.

13. A securement device as claimed in claim 12 wherein the primary anchor pad portion is connected with the secondary anchor pad portion by an anchor pad web portion extending between the primary anchor pad portion and the secondary anchor pad portion.

14. A securement device as claimed in claim 1 wherein the anchor pad comprises an adhesive for adhering the securement device to the patient.

15. A securement device as claimed in claim 14 wherein the anchor pad comprises a release film on the adhesive.

16. A securement device as claimed in claim 1, wherein the tubular medical article is a cable or a catheter.

17. A securement device for attaching a tubular medical article to a patient comprising:
   an primary anchor pad attachable to the patient;
   a base on the anchor pad for receiving the tubular medical article;
   a cap mountable on the base at a mounting defined between the base and the cap, the cap being rotatable on the base between a tubular medical article receiving position and a tubular medical article gripping position and comprising a slot for receiving the tubular medical article in the tubular medical article receiving position and gripping the tubular medical article in the tubular medical article gripping position;
   a secondary anchor pad attachable to the patient; and
   a fastener mountable on the secondary anchor pad for detachably fastening the tubular medical device;
   wherein the slot comprises first and second oppositely disposed, substantially helical slot portions in a sidewall of the cap, and
   wherein the helical slot portions comprise an upright slot element and a helical slot element contiguous with the upright slot element in the sidewall, and
   wherein the upright slot elements are connected by a transverse slot element, wherein the helical slot elements taper inwardly continuously towards a slot end in the sidewall, and wherein the tubular medical device is configured to extend between the fastener and the slot when in a secured position.

18. The securement device of claim 17, wherein the cap is configured to rotate 90 degrees between the tubular medical article receiving position and the tubular medical article gripping position.

19. A securement device for attaching a tubular medical article to a patient comprising:
   an anchor pad attachable to the patient;
   a base on the anchor pad for receiving the tubular medical article, and
   a screw cap mountable on the base at a mounting defined between the base and the cap, the cap being helically rotatable on the base between a tubular medical article receiving position and a tubular medical article gripping position and comprising a slot for receiving the tubular medical article in the tubular medical article receiving position and gripping the tubular medical article in the tubular medical article gripping position, wherein the slot comprises first and second oppositely disposed substantially helical slot portions in a sidewall of the cap, wherein each of the helical slot portions comprise an upright slot element and a helical slot element contiguous with the upright slot element in the sidewall, wherein the upright slot elements are connected by a transverse slot element, and wherein the helical slot elements taper inwardly continuously towards a slot end in the sidewall.

20. The securement device of claim 19, wherein the base includes a groove-like thread for guiding movement of the cap, the groove-like thread having a straight top portion and a helical bottom portion.

* * * * *

UNITED STATES PATENT AND TRADEMARK OFFICE
CERTIFICATE OF CORRECTION

PATENT NO. : 11,896,784 B2
APPLICATION NO. : 17/259490
DATED : February 13, 2024
INVENTOR(S) : Aidan G. O'Sullivan et al.

Page 1 of 1

It is certified that error appears in the above-identified patent and that said Letters Patent is hereby corrected as shown below:

In the Claims

Column 8, Line 45, Claim 9, delete "5" and insert --6--.

Signed and Sealed this
Seventh Day of May, 2024

Katherine Kelly Vidal
*Director of the United States Patent and Trademark Office*